US008460201B2

(12) United States Patent
Breeuwer

(10) Patent No.: US 8,460,201 B2
(45) Date of Patent: Jun. 11, 2013

(54) VISUALIZATION OF STRESS LEVEL CARDIAC FUNCTIONAL ANALYSIS RESULTS

(75) Inventor: Marcel Breeuwer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1173 days.

(21) Appl. No.: 12/375,028

(22) PCT Filed: Jul. 23, 2007

(86) PCT No.: PCT/IB2007/052915
§ 371 (c)(1),
(2), (4) Date: Jan. 26, 2009

(87) PCT Pub. No.: WO2008/012755
PCT Pub. Date: Jan. 31, 2008

(65) Prior Publication Data
US 2010/0022901 A1     Jan. 28, 2010

(30) Foreign Application Priority Data
Jul. 26, 2006   (EP) .................................... 06117839

(51) Int. Cl.
*A61B 5/02*        (2006.01)
*A61N 1/362*     (2006.01)
*A61N 1/00*       (2006.01)

(52) U.S. Cl.
USPC ................................ 600/508; 600/16; 607/9

(58) Field of Classification Search
USPC ................................. 600/16, 508, 513; 607/9
See application file for complete search history.

(56) References Cited

U.S. PATENT DOCUMENTS

| 2003/0083586 A1* | 5/2003 | Ferek-Petric | 600/512 |
| 2004/0087853 A1 | 5/2004 | Fujisawa | |
| 2004/0176679 A1* | 9/2004 | Murphy et al. | 600/407 |
| 2006/0058610 A1 | 3/2006 | Olstad | |
| 2006/0069322 A1* | 3/2006 | Zhang et al. | 600/512 |

OTHER PUBLICATIONS

Andrews, L.T., Klinger, J.W., Begeman, M.S., Zeiss, J., Leighton, R.F. Vizsualization of Cardiac Magnetic Resonance Images with Color Encoded 2D and 3D Functional Images, 1990, IEEE.*

Otto Muzik, et al; Automated Region Definition for Cardiac Nitrogen-13-Ammonia PET Imaging, Journal of Nuclear Medicine, vol. 34, No. 2, Feb. 1993, USA, pp. 336-344, ISSN 0161-5505.

(Continued)

*Primary Examiner* — Niketa Patel
*Assistant Examiner* — William Levicky

(57) ABSTRACT

The invention relates to a system (100) for visualizing a cardiac parameter at a plurality of positions in a myocardium and at a plurality of stress levels, the system comprising a determination unit (110) for determining a value of the cardiac parameter at a position from the plurality of positions in the myocardium and at a stress level from the plurality of stress levels on the basis of stress level cardiac functional data, and a visualization unit (120) for visualizing the determined value of the cardiac parameter by displaying a point in a viewing plane. The visualized points are defined by their polar coordinates in a polar coordinate system in the viewing plane. A radial coordinate of the point visualizes the determined value of the cardiac parameter. An angular coordinate of the point visualizes an angular coordinate of the position in the myocardium in a cylindrical coordinate system. Thus, the system allows easy numerical comparison of local myocardial contractions at different stress level values.

20 Claims, 5 Drawing Sheets

OTHER PUBLICATIONS

K. Hicks, et al; Automated Quantitation of Three-Dimensional Cardiac Positron Emission Tomography for Routine Clinical Use, Journal of Nuclear Medicine, Nov. 1989, USA, vol. 30, No. 11, pp. 1787-1797, ISSN 0161-5505.

Manuel D. Cerqueira, et al; Standardized Myocardial Segmentation and Nomenclature for Tomographic Imaging of the Heart: AHA Scientific Statement, vol. 105, pp. 539-542, Jan. 29, 2002, ISSN: 1524-4539.

* cited by examiner

VISUALIZATION OF STRESS LEVEL CARDIAC FUNCTIONAL ANALYSIS RESULTS

FIELD OF THE INVENTION

The invention relates to the field of visualization of medical image data and more specifically to the visualization of multiple stress level cardiac functional analysis results.

BACKGROUND OF THE INVENTION

Visualizing multiple stress level cardiac functional analysis results is described by M. Breeuwer in an article entitled "Quantification of atherosclerotic heart disease with cardiac MRI" in Medica Mundi, vol. 49 no. 2, pages 30-38, 2005, hereinafter referred to as Ref. 1. The article describes a number of parameters for quantifying a myocardial contractile function. For example, a parameter for quantifying the myocardial contraction may be wall thickening $WT=((W_{ES}-W_{ED})/W_{ED})\,100\%$, where $W_{ED}$ is the wall thickness at end diastole and $W_{ES}$ is the wall thickness at end systole, Wall thickening can be determined locally as a value at a position in the myocardium or as an average per myocardial segment. A standardized myocardial segmentation is described in the American Heart Association (AHA) Scientific Statement entitled "Standardized Myocardial Segmentation and Nomenclature for Tomographic Imaging of the Heart" by M. D. Cerqueira et al, in Circulation 2002, vol. 105, pages 539-542. A decrease in wall thickening with increasing cardiac stress may be an indication of ischemia, i.e. an insufficient blood supply to the heart muscle, whereas the total absence of wall thickening at all stress levels may indicate infarction, i.e. starvation of myocardial tissue. Furthermore, the absence of wall thickening at rest and the recovery of wall thickening at low stress levels may indicate hibernating myocardium, i.e. viable myocardium that does not contract at rest. To simplify the interpretation of the functional parameters such as wall thickening, the parameters are visualized using bulls-eye plots. The bulls-eye plots represent a parameter such as wall thickening assigned to as position in three dimensions by a two-dimensional plot. A color or a shade of gray may represent a value of the wall thickening. The inner circle corresponds to the apex of the left ventricle and the rings correspond to slices perpendicular to the left ventricular long axis. A shortcoming of this approach to visualizing multiple stress level cardiac functional analysis results is that the user cannot easily numerically compare local myocardial contractions at different stress levels. To realize such a numerical comparison, the user must retrieve numerical analysis reports and combine the numbers in these reports, e.g. by transferring these numbers into an excel spreadsheet and plotting a graph. This is a tedious and time-consuming task.

SUMMARY OF THE INVENTION

It would be advantageous to visualize multiple stress level cardiac functional analysis results in a way that allows easy numerical comparison of local myocardial contractions at different stress levels.

To better address this concern, in an aspect of the invention, a system for visualizing a cardiac parameter at a plurality of positions in a myocardium and at a plurality of stress levels, comprises:

a determination unit for determining a value of the cardiac parameter at a position from the plurality of positions in the myocardium and at a stress level from the plurality of stress levels on the basis of stress level cardiac functional data; and a visualization unit for visualizing the determined value of the cardiac parameter by displaying a point in a viewing plane, where in a polar coordinate system in the viewing plane:

a radial coordinate of the point visualizes the determined value of the cardiac parameter; and an angular coordinate of the point visualizes an angular coordinate of the position in the myocardium in a cylindrical coordinate system.

The stress level cardiac functional data comprises, for example, the wall thickness at end diastole and the wall thickness at end systole at a plurality of positions in a myocardium and at a plurality of stress levels. The determination unit is arranged to compute the wall thickening at the plurality of positions in a myocardium and at the plurality of stress levels, based on the stress level cardiac functional data. The visualization unit is arranged to visualize the computed values of the cardiac parameter by plotting a plurality of points in the viewing plane. Each point in the viewing plane corresponds to a position from the plurality of positions in a myocardium and to a stress level from the plurality of stress levels. In a polar coordinate system in the viewing plane, the radial coordinate of each point is substantially proportional to the determined value of wall thickening, and the angular coordinate of each point is substantially equal to an angular coordinate of the corresponding position from the plurality of positions in the myocardium in a cylindrical coordinate system. The cylindrical axis of the cylindrical coordinate system may be substantially identical with the long axis of the left ventricle. The visualized plurality of positions in the myocardium is comprised in a number of slices of the heart substantially perpendicular to the cylindrical axis of the cylindrical coordinate system, i.e. to the long axis of the left ventricle. In the case when the plurality of positions in the myocardium is comprised in the wall of the left ventricle, the points corresponding to a particular stress level and to positions comprised in a particular slice from the number of slices form a closed curve that visualizes the left ventricle wall thickening in the slice at the stress level. Hence, the system allows easy numerical comparison of local myocardial contractions at different stress levels.

In an embodiment of the system, the plurality of positions in the myocardium is comprised in a slice of the myocardium substantially perpendicular to a cylindrical axis of the cylindrical coordinate system. The cylindrical axis may be substantially identical with the long axis of the left ventricle and the slice may be substantially perpendicular to the long axis of the left ventricle. Assuming that the slice is relatively thin, e.g. 1 mm thick, the points corresponding to a certain stress level form a closed curve that visualizes the cardiac parameter in the slice of the myocardium at the certain stress level. This embodiment allows comparing determined values of the cardiac parameter at different stress levels in a slice of the myocardium.

In an embodiment of the system, the system further comprises:

an indication unit for indicating an angle in the polar coordinate system; and a plot unit for plotting a graph, based on positions from the plurality of positions in the myocardium which have angular coordinates substantially equal to the indicated angle.

The angle may be interactively selected by a user using the indication unit of the system. Plotting the graph, based on positions from the plurality of positions in the myocardium which have angular coordinates substantially equal to the indicated angle, allows visualizing how the determined values of the cardiac parameter at the indicated angle depend on stress level values.

In an embodiment of the system, the system further comprises an image display unit for displaying the slice of the myocardium at a stress level from the plurality of stress levels. Hence, the system allows linking the visualized points, based on the determined values of the cardiac parameter with an image of the respective slice of the myocardium. The visualized points may indicate a suspicious region of the slice of the myocardium. The user of the system, such as a physician, is thus enabled to view the suspicious region of the slice of the myocardium in the image.

In an embodiment of the system, the system further comprises a computation unit for computing an average of the cardiac parameter over a set of positions from the plurality of positions in the myocardium at a stress level from the plurality of stress levels. The set of positions in the myocardium may comprise positions from a myocardial segment recommended by the AHA. These segments are important in many practical clinical applications. Therefore, knowing the average of the cardiac parameter over a set of positions comprised in the myocardial segment may be very useful for a user of the system, such as a physician. In another embodiment, the set of positions from the plurality of positions in the myocardium may comprise positions from a plurality of slices and having angular coordinates, defined in a cylindrical coordinate system, from a user-defined range of angular coordinates.

In a further aspect of the invention, an image acquisition apparatus comprises a system for visualizing a cardiac parameter at a plurality of positions in a myocardium and at a plurality of stress levels, the system comprising:
  a determination unit for determining a value of the cardiac parameter at a position from the plurality of positions in the myocardium and at a stress level from the plurality of stress levels on the basis of stress level cardiac functional data; and
  a visualization unit for visualizing the determined value of the cardiac parameter by displaying a point in a viewing plane, where in a polar coordinate system in the viewing plane:
    a radial coordinate of the point visualizes the determined value of the cardiac parameter; and
    an angular coordinate of the point visualizes an angular coordinate of the position in the myocardium in a cylindrical coordinate system.

In a further aspect of the invention, a workstation comprises a system for visualizing a cardiac parameter at a plurality of positions in a myocardium and at a plurality of stress levels, the system comprising:
  a determination unit for determining a value of the cardiac parameter at a position from the plurality of positions in the myocardium and at a stress level from the plurality of stress levels on the basis of stress level cardiac functional data; and
  a visualization unit for visualizing the determined value of the cardiac parameter by displaying a point in a viewing plane, where in a polar coordinate system in the viewing plane:
    a radial coordinate of the point visualizes the determined value of the cardiac parameter; and
    an angular coordinate of the point visualizes an angular coordinate of the position in the myocardium in a cylindrical coordinate system.

In a further aspect of the invention, a method of visualizing a cardiac parameter at a plurality of positions in a myocardium and at a plurality of stress levels comprises:
  a determination step for determining a value of the cardiac parameter at a position from the plurality of positions in the myocardium and at a stress level from the plurality of stress levels on the basis of stress level cardiac functional data; and
  a visualization step for visualizing the determined value of the cardiac parameter by displaying a point in a viewing plane, where
  in a polar coordinate system in the viewing plane:
    a radial coordinate of the point visualizes the determined value of the cardiac parameter; and
    an angular coordinate of the point visualizes an angular coordinate of the position in the myocardium in a cylindrical coordinate system.

In a further aspect of the invention, a computer program product to be loaded by a computer arrangement comprises instructions for visualizing a cardiac parameter at a plurality of positions in a myocardium and at a plurality of stress levels, the computer arrangement comprising a processing unit and a memory, the computer program product, after being loaded, providing said processing unit with the capability to carry out the following tasks:
  determining a value of the cardiac parameter at a position from the plurality of positions in the myocardium and at a stress level from the plurality of stress levels on the basis of stress level cardiac functional data; and
  visualizing the determined value of the cardiac parameter by displaying a point in a viewing plane, where
  in a polar coordinate system in the viewing plane:
    a radial coordinate of the point visualizes the determined value of the cardiac parameter; and
    an angular coordinate of the point visualizes an angular coordinate of the position in the myocardium in a cylindrical coordinate system.

Modifications and variations thereof, of the image acquisition apparatus, of the workstation, of the method, and/or of the computer program product, which correspond to modifications of the system and variations thereof being described, can be carried out by a skilled person on the basis of the present description.

The skilled person will appreciate that the method may be applied to three-dimensional (3D) image data generated by various acquisition modalities such as, but not limited to, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

The same reference numerals are used to denote similar parts throughout the Figures.

DETAILED DESCRIPTION OF EMBODIMENTS

Figure 1:
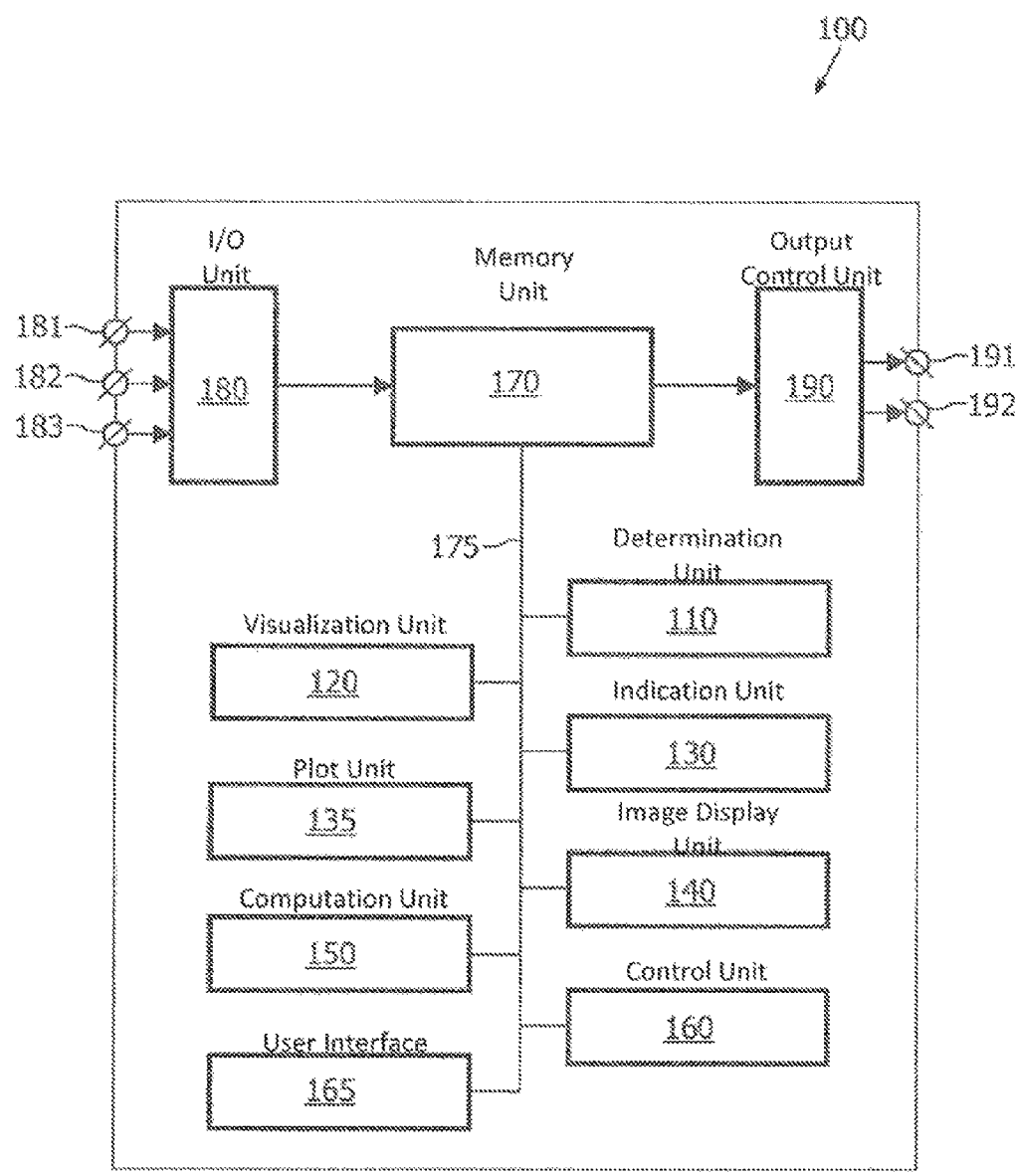
FIG. 1 schematically shows a block diagram of an exemplary embodiment of the system.

FIG. 1 schematically shows a block diagram of an exemplary embodiment of the system 100 for visualizing a cardiac parameter at a plurality of positions in a myocardium and at a plurality of stress levels, the system 100 comprising:

- a determination unit 110 for determining a value of the cardiac parameter at a position from the plurality of positions in the myocardium and at a stress level from the plurality of stress levels on the basis of stress level cardiac functional data; and
- a visualization unit 120 for visualizing the determined value of the cardiac parameter by displaying a point in a viewing plane, where in a polar coordinate system in the viewing plane:
- a radial coordinate of the point visualizes the determined value of the cardiac parameter; and
- an angular coordinate of the point visualizes an angular coordinate of the position in the myocardium in a cylindrical coordinate system.

The exemplary embodiment of the system 100 further comprises the following units:

- an indication unit 130 for indicating an angle in the polar coordinate system;
- a plot unit 135 for plotting a graph, based on positions from the plurality of positions in the myocardium, which have angular coordinates substantially equal to the indicated angle;
- an image display unit 140 for displaying the slice of the myocardium at a stress level from the plurality of stress levels;
- a computation unit 150 for computing an average of the cardiac parameter over a set of positions from the plurality of positions in the myocardium at a stress level from the plurality of stress levels;
- a control unit 160 for controlling the workflow in the system 100;
- a user interface 165 for communicating with a user of the system 100; and
- a memory unit 170 for storing data.

In the exemplary embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In the exemplary embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In the exemplary embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, stress level cardiac functional data. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, determined values of the cardiac parameter, the respective positions from the plurality of positions in the myocardium, and the respective stress levels from the plurality of stress levels. The memory unit 170 is also arranged to receive data from and deliver data to the units of the system 100 comprising the determination unit 110, the visualization unit 120, the indication unit 130, the plot unit 135, the image display unit 140, the computation unit 150, the control unit 160, and the user interface 165, via a memory bus 175. The memory unit 170 is further arranged to make the output data available to external devices via any of the output connectors 191 and 192. Storing the data from the units of the system 100 in the memory unit 170 may advantageously improve the performance of the units of the system 100 as well as the rate of transfer of the output data from the units of the system 100 to external devices.

Alternatively, the system 100 may not comprise the memory unit 170 and the memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In the exemplary embodiment of the system 100 shown in FIG. 1, the system 100 comprises a control unit 160 for controlling the workflow in the system 100. The control unit may be arranged to receive control data from and provide control data to the units of the system 100. For example, after filling a buffer comprised in the memory unit 170 with values of the cardiac parameter determined by the determination unit 110, the determination unit 110 may be arranged to provide input control data "the values of the cardiac parameter are determined" to the control unit 160, and the control unit 160 may be arranged to provide output control data "start visualizing the determined values of the cardiac parameter" to the visualization unit 120, requesting the visualization unit 120 to start visualizing the values of the cardiac parameter. Alternatively, a control function may be implemented in another unit of the system 100.

In the exemplary embodiment of the system 100 shown in FIG. 1, the system 100 comprises a user interface 165 for communicating with the user of the system 100. The user interface 165 may be arranged to accept a user input for indicating an angle in the polar coordinate system in the viewing plane, for example. Further, the user interface 165 may be arranged to interact with the user in order to allow the user to decide which data to visualize and in what form, e.g. to allow the user to select a slice of the myocardium comprising positions to be visualized. Optionally, the user interface may receive a user input for selecting a mode of operation of the system 100, such as a mode for visualizing a particular cardiac parameter such as wall thickening or wall motion. The skilled person will understand that more functions may be advantageously implemented in the user interface 165 of the system 100.

The stress level cardiac functional data may comprise, for example, myocardial wall thickness at end diastole and myocardial wall thickness at end systole at a plurality of positions in a myocardium and at a plurality of stress levels. To induce the stress, a chemical stress agent such as dobutamine is injected into the bloodstream before the acquisition of image data. In a Cartesian system of coordinates, a position P in the myocardium is described by three Cartesian coordinates x, y, z. The z axis of the Cartesian system of coordinates may be advantageously aligned with the long axis of the left ventricle which transects the apex and the center of the mitral valve (see Ref. 2). In a cylindrical system of coordinates with the cylindrical axis substantially identical with the long axis of the left ventricle, a position P in the myocardium is described by three cylindrical coordinates: a height h=z, an angle $\alpha$, also referred to as an angular coordinate or as an azimuthal angle, and a radius r, also referred to as a radial coordinate. The height h is determined by the crossing of the cylindrical axis by a section plane comprising the position P and extending perpendicularly to the cylindrical axis. The relationship between the Cartesian coordinate and the cylindrical coordinate of the position P in the section plane is determined by the relations: $x=r \cos \alpha$ and $y=r \sin \alpha$. The myocardial wall thickness at the position P may be defined as the length of the shortest interval stretching between the outer surface and the inner surface of the myocardial wall along a line crossing the position P. Other definitions are also possible. Typically, the position P is a position on a predetermined surface of the myocardium, e.g. an outer surface of the myocardium or an inner surface of the myocardium.

Alternatively, the stress level cardiac functional data may comprise other data such as cylindrical coordinates of positions on the outer surface and on the inner surface of the myocardial wall at a plurality of phases of a cardiac cycle and at a plurality of stress levels. The skilled person will understand that the described stress level cardiac functional data illustrate the invention and do not limit the scope of the claims.

The stress level cardiac functional data is used for visualizing the results of quantitative cardiac functional analysis of said stress level cardiac functional data. The results may comprise a cardiac parameter such as, but not limited to, local myocardial wall thickening and wall motion. The system of the invention will be explained using wall thickening determined on the basis of stress level cardiac functional data comprising the wall thickness at end diastole and the wall thickness at end systole at a plurality of positions on the outer surface of the myocardial wall of the left ventricle and at a plurality of stress levels. The skilled person will understand that the scope of the claims is not limited by the choice of the cardiac parameter.

The determination unit 110 of the system 100 is arranged to determine a value of the cardiac parameter at a position from the plurality of positions in the myocardium and at a stress level from the plurality of stress levels on the basis of the stress level cardiac functional data. The exemplary cardiac parameter is myocardial wall thickening. The determination unit 110 is arranged to compute the wall thickening at the position from the plurality of positions in the myocardium and at the stress level from the plurality of stress levels on the basis of the stress level cardiac functional data. The wall thickening WT is defined by $WT=((W_{ES}-W_{ED})/W_{ED}) \cdot 100\%$, where $W_{ED}$ is the wall thickness at end diastole and $W_{ES}$ is the wall thickness at end systole.

The visualization unit 120 of the system 100 is arranged to visualize the determined value of the cardiac parameter by displaying a point in a viewing plane. In a polar coordinate system in the viewing plane, the radial coordinate of the point is substantially proportional to the computed value of the cardiac parameter, and the angular coordinate of the point is substantially equal to the angular coordinate of the position in the myocardium in a cylindrical coordinate system. The cylindrical axis of the cylindrical coordinate system may be substantially identical with the long axis of the left ventricle. The displayed point in the viewing plane corresponds to the position from the plurality of positions in the myocardium and to the stress level from the plurality of stress levels.

The system 100 may be further arranged to determine a plurality of values of the cardiac parameter for the plurality of positions in the myocardium and for the plurality of stress levels. Each value from the plurality of determined values of the cardiac parameter will be represented by a point in the viewing plane. The plurality of positions in the myocardium may be comprised in a number of planar sections or in a number of slices of the left ventricle substantially perpendicular to the left ventricular long axis. The slice of a myocardium is a region comprised between two section planes. Points corresponding to positions in a section plane or in a thin slice of the myocardium and further corresponding to one stress level lie on a closed curve that visualizes the left ventricle wall thickening at said section plane or at said thin slice of the myocardium at said stress level. Multiple closed curves in the viewing plane may correspond to multiple section planes or multiple thin slices, and/or to multiple stress levels. Different curves may be visualized using different colors, grayscale shades, and/or dashed lines. Optionally, markers and/or annotations may be added to improve readability of the results of the quantitative cardiac functional analysis of the stress level cardiac functional data.

In an embodiment of the system, the plurality of positions in the myocardium is comprised in a slice of the myocardium substantially perpendicular to a cylindrical axis of the cylindrical coordinate system. The cylindrical axis of the cylindrical coordinate system may be substantially identical with the long axis of the left ventricle. Thus, the slice is substantially perpendicular to the long axis of the left ventricle. The points corresponding to a certain stress level form a closed curve that visualizes the determined values of the cardiac parameter in the slice of the myocardium at the certain stress level. This embodiment allows easy comparison of the determined values of the cardiac parameter at positions comprised in one slice of the myocardium at different stress levels.

Figure 2:
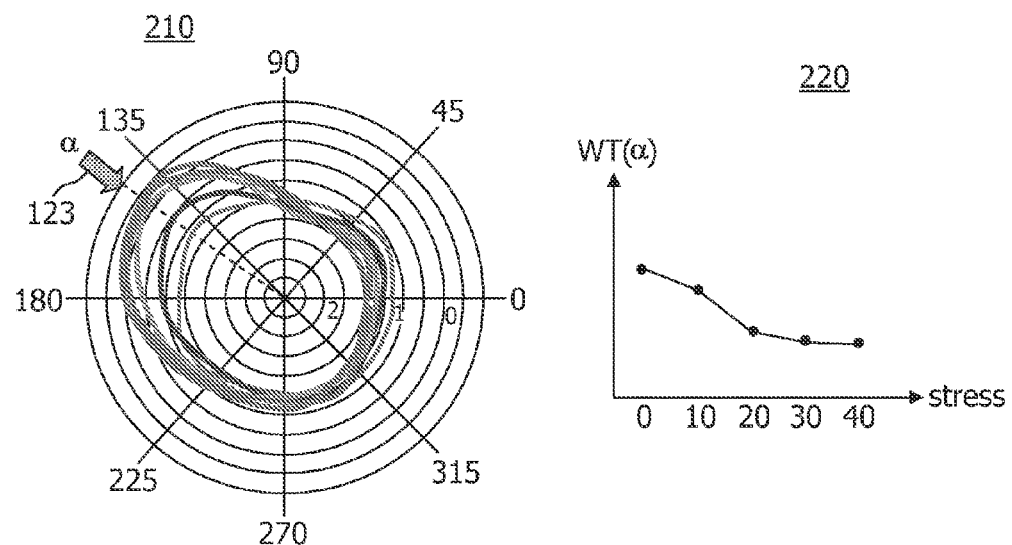
FIG. 2 shows an exemplary viewing plane illustrating left ventricular myocardial wall thickening in a slice of an ischemic heart with occluded left anterior descending coronary artery.
Figure 3:
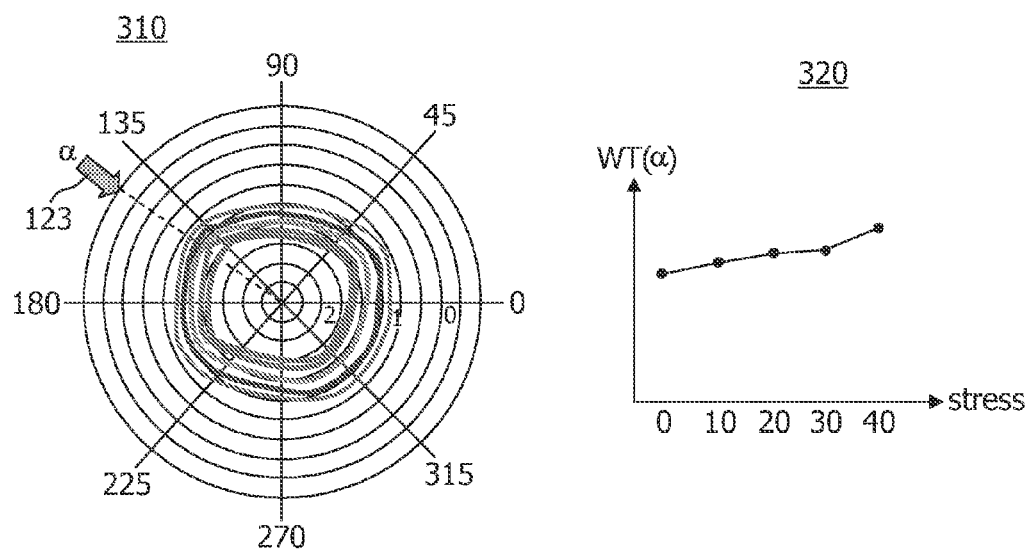
FIG. 3 shows an exemplary viewing plane illustrating left ventricular myocardial wall thickening in a slice of a normal heart.

FIG. 2 shows an exemplary viewing plane illustrating left ventricular myocardial wall thickening in a slice of an ischemic heart with occluded left anterior descending coronary artery (LAD). Each closed curve in a first radial graph 210 represents a different stress level. FIG. 3 shows an exemplary viewing plane illustrating left ventricular myocardial wall thickening in a slice of a normal heart. Each closed curve in a second radial graph 310 represents a different stress level. A comparison of the closed curves shown in the first radial graph 210 with the curves shown in the second radial graph 310 illustrates that specific coronary-artery occlusions may be associated with specific shapes of the curves visualized in the viewing plane. Thus, the effect of the occlusion of the myocardium at increasing stress can be directly assessed from the first radial graph 210 shown in FIG. 2.

In an embodiment of the system, the system further comprises:
an indication unit 130 for indicating an angle in the polar coordinate system; and
a plot unit 135 for plotting a graph, based on positions from the plurality of positions in the myocardium which have angular coordinates substantially equal to the indicated angle.

The indication unit 130 may be integrated with the user interface 165. The angle may be indicated based on a user input. An arrow 123 in FIG. 2 shows the indicated angle α in the polar coordinate system. The values of the wall thickening determined at different stress level values at positions comprised in the slice of myocardium having the polar coordinate substantially identical with the indicated angle are displayed in a first graph 220 plotted by the plot unit 135, as shown in FIG. 2. Similarly, the arrow 123 in FIG. 3 shows the indicated angle α in the polar coordinate system. The values of the wall thickening determined at different stress level values at positions comprised in the slice of myocardium having the polar coordinate substantially identical with the indicated angle are displayed in a second graph 320 plotted by the plot unit 135, as shown in FIG. 3. Plotting the graph, based on positions from the plurality of positions in the myocardium which have angular coordinates substantially equal to the indicated angle provides yet one more way of visualizing how the determined values of the cardiac parameter at the indicated angle depend on the stress level.

In an embodiment of the system, the system further comprises an image display unit 140 for displaying the slice of the myocardium at a stress level from the plurality of stress levels. For example, the slice of the myocardium at end diastole and the slice of the myocardium at end systole may be shown. Based on the values of wall thickening indicating a suspicious region of the slice of the left ventricular myocardium, a user such as a cardiologist may view the suspicious region and search for more clues about the condition of a patient's heart.

In an embodiment of the system, the system further comprises a computation unit 150 for computing an average of the cardiac parameter over a set of positions from the plurality of positions in the myocardium at a stress level from the plurality of stress levels. The set of positions on the left ventricular myocardium may comprise positions from a myocardial segment described in Ref. 2 and recommended by the AHA. The average of the cardiac parameter may be shown in numerical form, e.g. in a table or in a 17-segment left ventricular diagram proposed by the AHA. In another embodiment, the set of positions from the plurality of positions in the myocardium may comprise positions from a plurality of slices and having angular coordinates, defined in a cylindrical coordinate system, from a user-defined range of angular coordinates. The skilled person will appreciate that the set of positions from the plurality of positions in the myocardium may be defined in any way that meets requirements of the user.

The skilled person will further understand that other embodiments of the system 100 are also possible. It is possible, among other things, to redefine the units of the system and to redistribute their functions. For example, in an embodiment of the system 100, the functions of the control unit 160 may be assigned to other units of the system 100. In a further embodiment of the system 100, there can be a plurality of determination units replacing the determination unit 110 of the previous embodiments of the system 100, with each determination unit being arranged to determine values of a different cardiac parameter. The selection of the determination unit to be employed by the system 100 may be based on a user input.

The units of the system 100 may be implemented using a processor. Normally, their functions are performed under control of a software program product. During execution, the software program product is normally loaded into a memory, like a RAM, and executed from said memory. The program may be loaded from a background memory, like a ROM, hard disk, or magnetic and/or optical storage means, or may be loaded via a network like the Internet. Optionally, an application specific integrated circuit may provide the described functionality.

Figure 4:
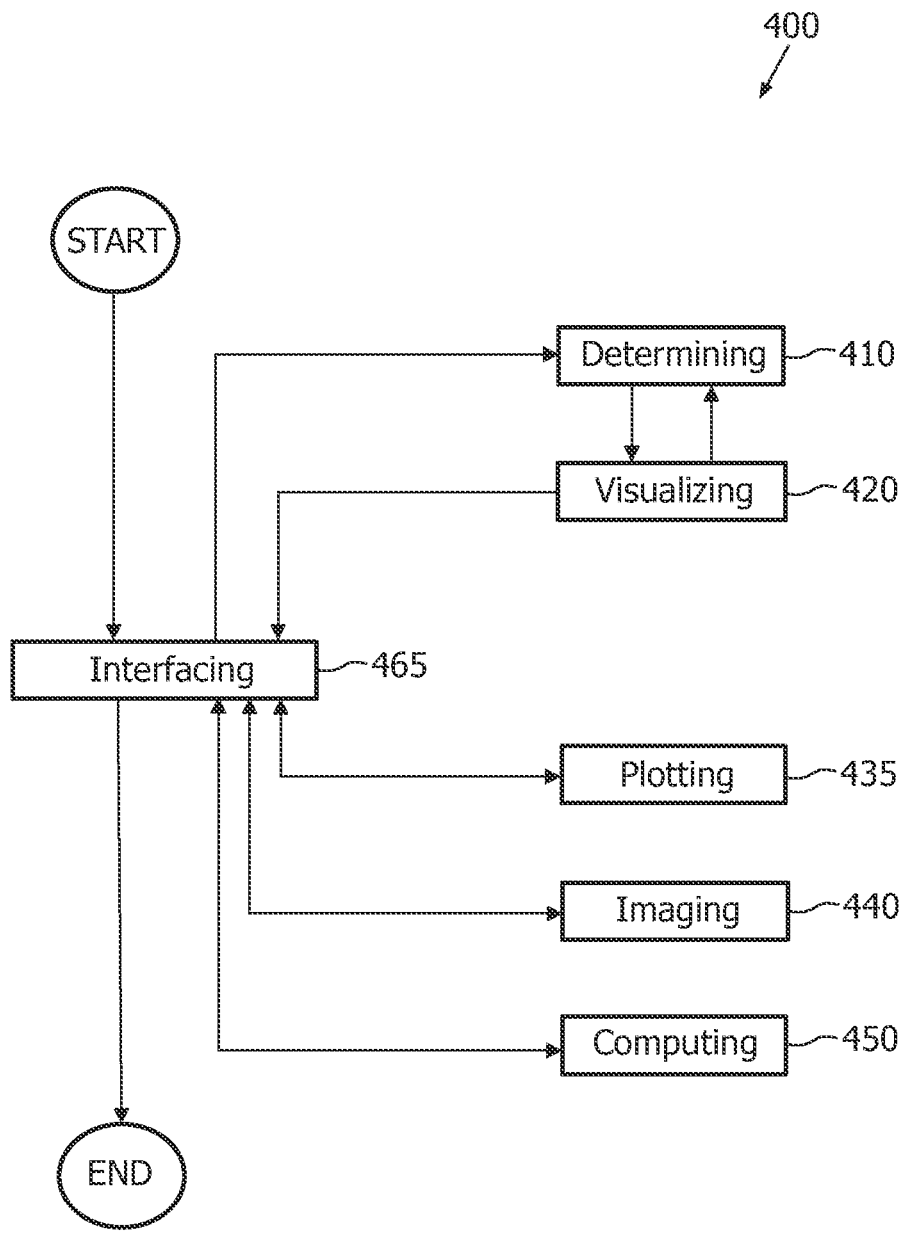
FIG. 4 shows a flowchart of an exemplary implementation of the method.

FIG. 4 shows a flowchart of an exemplary implementation of the method 400 of visualizing a cardiac parameter at a plurality of positions in a myocardium and at a plurality of stress levels. In this implementation, the method 400 begins at an interface step 465 for receiving a user input, e.g. the name of a file comprising stress level cardiac functional data. After determining a plurality of positions in the myocardium and a plurality of stress levels, e.g. based on the stress level cardiac functional data, the method 400 continues to a determination step 410 for determining a value of the cardiac parameter at a position from the plurality of positions in the myocardium and at a stress level from the plurality of stress levels on the basis of the stress level cardiac functional data. After the determination step 410, the method 400 continues to a visualization step 420 for visualizing the determined value of the cardiac parameter by displaying a point in a viewing plane. In a polar coordinate system in the viewing plane, a radial coordinate of the point visualizes the determined value of the cardiac parameter and an angular coordinate of the point visualizes an angular coordinate of the position in the myocardium in a cylindrical coordinate system. After the visualization step 420, the method 400 returns to the determination step 410 to determine a next value of the cardiac parameter at a next position from the plurality of positions in the myocardium and at a next stress level from the plurality of stress levels. Then the method 400 continues to the visualization step 420 for visualizing the determined next value of the cardiac parameter by displaying a next point in the viewing plane. The method 400 oscillates between the determination step 410 and the visualization step 420 until values of the cardiac parameter for all positions from the plurality of positions in the myocardium and for all stress levels from the plurality of stress levels have been visualized. Next, the method continues to the interface step 465 for receiving a user input. The user may further decide which part of the stress level cardiac functional data is to be visualized and how to visualize the stress level cardiac functional data. After indicating an angle in the polar coordinate system, based on a user input received in the interface step 430, the method 400 continues to a plot step 440 for plotting a graph, based on positions from the plurality of positions in the myocardium which have angular coordinates substantially equal to the indicated angle. After the plot step 435, the method 400 returns to the interface step 465 for receiving a user input. After selecting a slice of the myocardium, based on a user input in the interface step 465, the method may continue to the determination step 410 for determining values of the cardiac parameter at positions comprised in the selected slice of the myocardium and subsequently to the visualization step 420 for visualizing the determined value of the cardiac parameter by displaying a point in the viewing plane. After visualizing values of the cardiac parameter in the selected slice, the method 400 returns to the interface step 465 for receiving a user input. Alternatively, after receiving a user input for selecting a stress level from the plurality of stress levels in the interface step 465, the method 400 may continue to an image display step 440 for displaying the selected slice of the myocardium at the selected stress level. After the image display step 440, the method 400 returns to the interface step 465 for receiving a user input. After selecting an input for computing an average of the cardiac parameter over a set of positions from the plurality of positions in the myocardium at a stress level from the plurality of stress levels, the method 400 continues to a computation step 450 for computing the average of the cardiac parameter over the set of positions from the plurality of positions in the myocardium at the stress level from the plurality of stress levels. After the computation step 450, the method 400 returns to the interface step 465 for receiving a user input. After the user has entered an input for terminating the method 400 in the interface step 465, the method 400 terminates.

The order of steps in the method 400 of computing an image comprising a first image and a second image is not mandatory, the skilled person may change the order of some steps or perform some steps concurrently, using threading models, multi-processor systems or multiple processes without departing from the concept as intended by the present invention. For example, in an implementation of the method 400, a plurality of values of the cardiac parameter may be computed concurrently in the determination step 410. Optionally, two or more steps of the method 100 of the current invention may be combined into one step. Optionally, a step of the method 100 of the current invention may be split into a plurality of steps. Some steps of the method 100 are optional and may be omitted.

Figure 5:
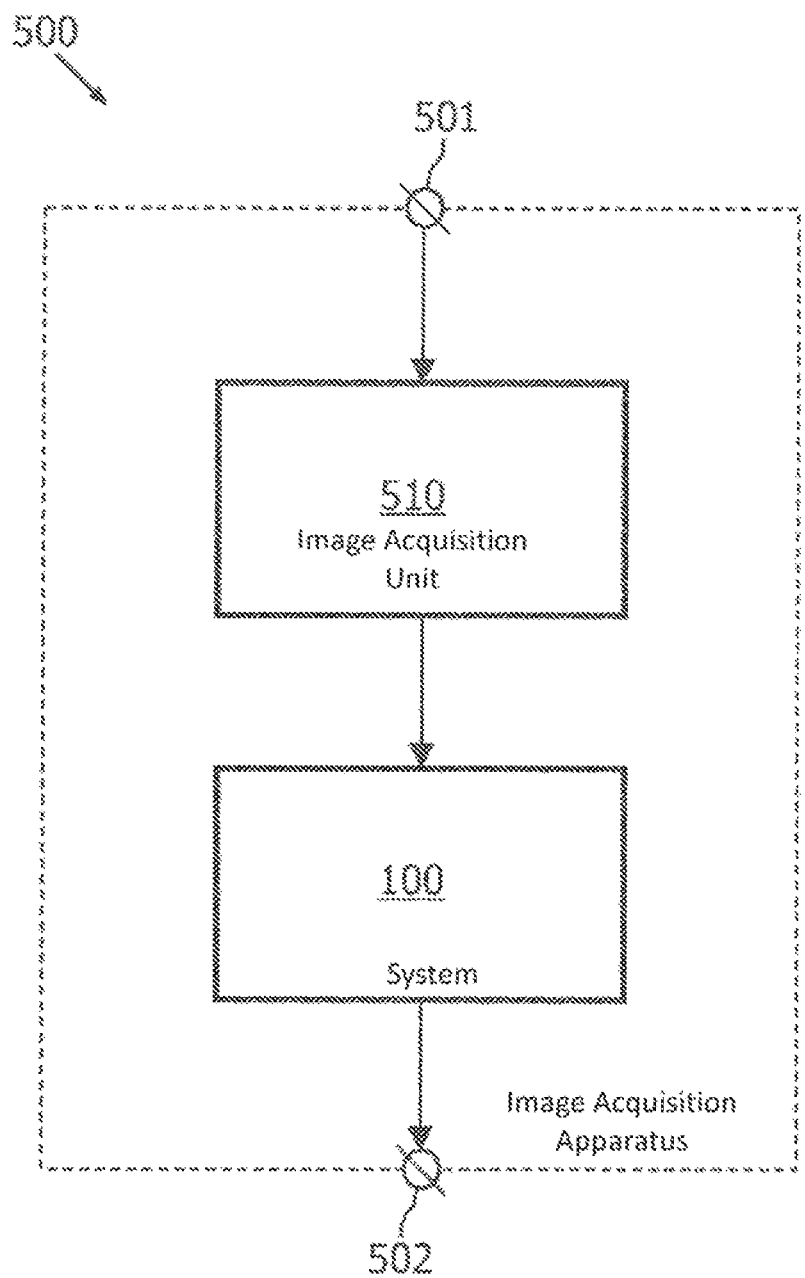
FIG. 5 schematically shows an exemplary embodiment of the image acquisition apparatus.

FIG. 5 schematically shows an exemplary embodiment of the image acquisition apparatus 500 employing the system 100, said image acquisition apparatus 500 comprising an image acquisition unit 510 connected via an internal connection with the system 100, an input connector 501, and an output connector 502. This arrangement advantageously increases the capabilities of the image acquisition apparatus 500 by providing said image acquisition apparatus 500 with advantageous capabilities of the system 100 for visualizing a cardiac parameter at a plurality of positions in a myocardium and at a plurality of stress levels. Examples of image acquisition apparatus comprise, but are not limited to, a CT system, an X-ray system, an MRI system, an US system, a PET system, a SPECT system, and a NM system.

Figure 6:
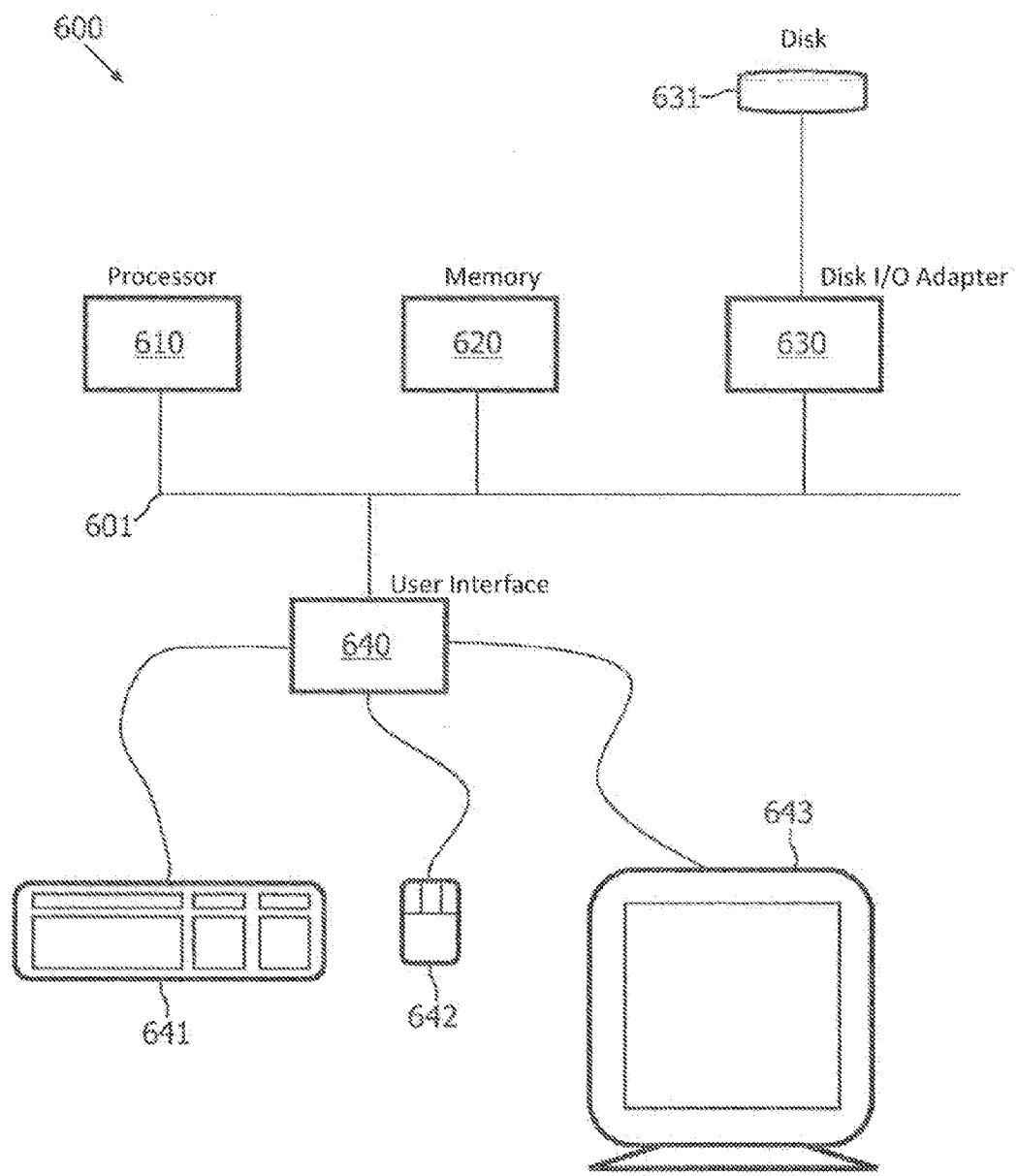
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. The skilled person will understand that there are numerous other embodiments of the workstation 600 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera, does not indicate any ordering. These words are to be interpreted as names.

The invention claimed is:

1. A system for visualizing a cardiac parameter at a plurality of positions in a myocardium and at a plurality of stress levels, the system comprising:
   a memory unit which receives and stores stress level cardiac functional data, the stress level cardiac functional data including cylindrical coordinates of positions on an outer surface and on an inner surface of a wall of the myocardium at a plurality of phases of a cardiac cycle and at a plurality of stress levels;
   a determination unit for determining a value of the cardiac parameter at a position from the plurality of positions in the myocardium and at a stress level from the plurality of stress levels on the basis of stress level cardiac functional data; and
   a visualization unit for visualizing the determined value of the cardiac parameter by displaying a point in a viewing plane, where in a polar coordinate system in the viewing plane;
   a radial coordinate of the point visualizes the determined value of the cardiac parameter; and
   an angular coordinate of the point visualizes an angular coordinate of the position in the myocardium in a cylindrical coordinate system.

2. The system as claimed in claim 1, wherein the plurality of positions in the myocardium are included in a slice of the myocardium substantially perpendicular to is cylindrical axis of the cylindrical coordinate system.

3. The system as claimed in claim 2, further including:
   an indication unit for indicating an angle in the polar coordinate system; and
   a plot unit for plotting a graph, based on positions from the plurality of positions in the myocardium which have angular coordinates substantially equal to the indicated angle.

4. The system as claimed in claim 2, further including an image display unit for displaying the slice of the myocardium at a stress level from the plurality of stress levels.

5. The system as claimed in claim 1, further including a computation unit for computing an average of the cardiac parameter over a set of positions from plurality of positions in the myocardium at a stress level from the plurality of stress levels.

6. An image acquisition apparatus comprising the system claimed in claim 1.

7. A workstation comprising the system as claimed in claim 1.

8. A method visualizing a cardiac parameter at a plurality of positions in a myocardium and at a plurality of stress levels, the method comprising:
    determining a value of the cardiac parameter at a position from the plurality of positions in the myocardium and at a stress level from the plurality of stress levels on the basis of stress level cardiac functional data; and
    visualizing the determined value of the cardiac parameter by displaying a point in a viewing plane, where in a polar coordinate system in the viewing plane:
        a radial coordinate of the point visualizes the determined value of the cardiac parameter; and
        an angular coordinate of the point visualizes an angular coordinate of the position in the myocardium in a cylindrical coordinate system.

9. The method as claimed in claim 8, wherein the plurality of positions in the myocardium are included in a slice of the myocardium substantially perpendicular to a cylindrical axis of the cylindrical coordinate system.

10. The method as claimed in claim 9, further including:
    indicating an angle in the polar coordinate system; and
    plotting a graph, based on positions from the plurality of positions in the myocardium which have angular coordinates substantially equal to the indicated angle.

11. The method as claimed in claim 8, wherein the stress level cardiac functional data includes cylindrical coordinates of positions en an outer surface and on an inner surface of the myocardium wall at a plurality of phases of a cardiac cycle and at a plurality of stress levels.

12. The method as claimed in claim 8, further
    computing an average of the cardiac parameter over a set of positions from the plurality of positions in the myocardium at a stress level from the plurality of stress levels.

13. The method as claimed in claim 8, further including:
    receiving stress level cardiac functional data from at least one of a data storage device and a user input; and
    storing the stress level cardiac functional data.

14. A non-transitory digital medium carrying a computer program product to be loaded by a computer arrangement, comprising instructions tor visualizing a cardiac parameter at a plurality of positions in a myocardium and at a plurality of stress levels, the computer arrangement comprising a processing unit and a memory, the computer program product, after being loaded, providing said processing unit with a capability to carry out the tasks of:
    determining a value of the cardiac parameter at a position from the plurality of positions in the myocardium and at a stress level from the plurality of stress levels on the basis of stress level cardiac functional data; and
    visualizing the determined value of the cardiac parameter by displaying a point in a viewing plane, where in a polar coordinate system in the viewing plane:
        a radial coordinate of the point visualizes the determined value of the cardiac parameter; and
        an angular coordinate of the point visualizes an angular coordinate of the position in the myocardium in a cylindrical coordinate system.

15. The non-transitory digital medium carrying a computer program product to he loaded by a computer arrangement as claimed in claim 14, wherein the plurality of positions in the myocardium are included in a slice of the myocardium substantially perpendicular to a cylindrical axis of the cylindrical coordinate system.

16. The non-transitory digital medium carrying is computer program product to be loaded by a computer arrangement as claimed in claim 15, further including instructions to carry out the task of:
    indicating an angle in the polar coordinate system; and
    plotting a graph, based on positions from the plurality of positions in the myocardium which have angular coordinates substantially equal to the indicated angle.

17. The non-transitory digital medium carrying a computer program product to be loaded by a computer arrangement as claimed in claim 15, further including instructions to carry out the task of:
    displaying the slice of the myocardium at a stress level from the plurality of stress levels on a display unit.

18. The non-transitory digital medium carrying a computer program product to be loaded by a computer arrangement as claimed in claim 14, further including instructions to carry out the task of:
    computing an average of the cardiac parameter over a set of positions from the plurality of positions in the myocardium at a stress level from the plurality of stress levels.

19. The non-transitory digital medium carrying a computer program product to be loaded by a computer arrangement as chimed in claim 14, wherein the stress level cardiac functional data includes cylindrical coordinates of positrons on an outer surface and on an inner surface of the myocardium wall at a plurality of phases of a cardiac cycle and at a plurality of stress levels.

20. The non-transitory digital medium carrying a computer program product to be loaded by a computer arrangement as claimed in claim 14, further including:
    receiving stress level cardiac functional data from at least one of a data storage device and a user input; and
    storing the stress level cardiac functional data.

* * * * *